United States Patent
Momeni et al.

(10) Patent No.: US 9,347,956 B2
(45) Date of Patent: May 24, 2016

(54) BIOMARKER AND USES THEREOF IN DIAGNOSIS, TREATMENT OF AUTISM

(75) Inventors: Naghi Momeni, Malmö (SE); Bengt L. Persson, Kalmar (SE)

(73) Assignee: Autism Biotech Limited, Reading, Berkshire (GB)

( * ) Notice: Subject to any disclaimer, the term of this patent is extended or adjusted under 35 U.S.C. 154(b) by 418 days.

(21) Appl. No.: 13/994,671

(22) PCT Filed: Dec. 13, 2011

(86) PCT No.: PCT/SE2011/051504
§ 371 (c)(1),
(2), (4) Date: Jun. 14, 2013

(87) PCT Pub. No.: WO2012/082056
PCT Pub. Date: Jun. 21, 2012

(65) Prior Publication Data
US 2013/0267441 A1   Oct. 10, 2013

Related U.S. Application Data

(60) Provisional application No. 61/423,636, filed on Dec. 16, 2010.

(30) Foreign Application Priority Data

Dec. 16, 2010   (SE) ...................................... 1051330

(51) Int. Cl.
| | |
|---|---|
| C40B 20/00 | (2006.01) |
| G01N 33/68 | (2006.01) |
| A61K 31/17 | (2006.01) |
| A61K 31/245 | (2006.01) |
| A61K 38/55 | (2006.01) |

(Continued)

(52) U.S. Cl.
CPC ............ *G01N 33/6896* (2013.01); *A61K 31/17* (2013.01); *A61K 31/245* (2013.01); *A61K 38/55* (2013.01); *A61K 38/57* (2013.01); *C07K 14/472* (2013.01); *C40B 20/00* (2013.01); *G01N 2800/28* (2013.01)

(58) Field of Classification Search
None
See application file for complete search history.

(56) References Cited

U.S. PATENT DOCUMENTS

2005/0048584 A1   3/2005   Lamping et al.

FOREIGN PATENT DOCUMENTS

| WO | 02/088174 A2 | 11/2002 |
|---|---|---|
| WO | 02/088707 A2 | 11/2002 |

(Continued)

OTHER PUBLICATIONS

International Search Report received for PCT Patent Application No. PCT/SE2011/051504, mailed on Mar. 21, 2012, 4 pages.

(Continued)

*Primary Examiner* — Christian Boesen
(74) *Attorney, Agent, or Firm* — Morrison & Foerster LLP

(57) ABSTRACT

A new biomarker, a peptide having sequence SSKITHRIH-WESASLLR*, wherein the side chain of the C-terminal arginine denoted with the asterisk is lacking the NH2- C=NH moiety normally present in the side chain. Usefulness of the biomarker in the diagnosis of neurological and/or neuropsychiatric disorders (in particular autism) is disclosed, as well as are methods for determining the concentration of the new biomarker and antibodies directed to the new biomarker. Treatment of autism, comprising administering a complement factor I inhibitor to the subject.

6 Claims, 11 Drawing Sheets

A

B

(51) Int. Cl.
*A61K 38/57* (2006.01)
*C07K 14/47* (2006.01)

(56) References Cited

FOREIGN PATENT DOCUMENTS

WO 02/088725 A2 11/2002
WO 2004/079371 A1 9/2004

OTHER PUBLICATIONS

Chauhan et al., "Increased Serum Complement C3 and C4 Levels in Autism: A Correlation with Severity and Language Disability", XP-002671086, Abstracts—L1-010P, 2005, pp. 492-493.

Gupta et al., "Brief Report: Dysregulated Immune System in Children with Autism: Beneficial Effects of Intravenous Immune Globulin on Autistic Characteristics", Journal of Autism and Developmental Disorders, vol. 26, No. 4, Aug. 1996, pp. 439-452.

Momeni et al., "High Complement Factor I Activity in the Plasma of Children with Autism Spectrum Disorders", Autism Research and Treatment, vol. 2012, Article ID 868576, 2012, pp. 1-6.

Tsiftsoglou et al., "Human Complement Factor I Does Not Require Cofactors for Cleavage of Synthetic Substrates", The Journal of Immunology, vol. 173, 2004, pp. 367-375.

Office Action Received for European Patent Application No. 11808394.8, mailed on May 21, 2014, 4 pages.

Corbett et al., "A Proteomic Study of Serum From Children with Autism Showing Differential Expression of Polipoproteins and Complement Proteins", Molecular Psychiatry, vol. 12, 2007, pp. 292-306.

A

B

SEQUENCE LISTING

```
<160> NUMBER OF SEQ ID NOS: 3

<210> SEQ ID NO 1
<211> LENGTH: 17
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: Modified C-terminal Arg: NH2-C=NH moiety lost
      from side chain (see Fig 1 for additional illustration).

<400> SEQUENCE: 1

Ser Ser Lys Ile Thr His Arg Ile His Trp Glu Ser Ala Ser Leu Leu
1               5                   10                  15

Arg

<210> SEQ ID NO 2
<211> LENGTH: 16
<212> TYPE: PRT
<213> ORGANISM: Homo sapiens

<400> SEQUENCE: 2

Ser Ser Lys Ile Thr His Arg Ile His Trp Glu Ser Ala Ser Leu Leu
1               5                   10                  15

<210> SEQ ID NO 3
<211> LENGTH: 17
<212> TYPE: PRT
<213> ORGANISM: Homo sapiens

<400> SEQUENCE: 3

Ser Ser Lys Ile Thr His Arg Ile His Trp Glu Ser Ala Ser Leu Leu
1               5                   10                  15

Arg
```

BIOMARKER AND USES THEREOF IN DIAGNOSIS, TREATMENT OF AUTISM

CROSS REFERENCE TO RELATED APPLICATIONS

This application is a U.S. National Phase patent application of PCT/SE2011/051504, filed Dec. 13, 2011, which claims priority to Swedish Patent Application No. 1051330-7, filed Dec. 16, 2010, and U.S. Provisional Patent Application No. 61/423,636, filed Dec. 16, 2010, each of which is hereby incorporated by reference in the present disclosure in its entirety.

TECHNICAL FIELD OF THE INVENTION

The present invention relates to biological peptides, methods for analysing such peptides, particularly in biological samples, and related methods of diagnosis for neurological and/or neuropsychiatric disorders, in particular autism. The present invention further relates to treatment of autism.

BACKGROUND TO THE INVENTION

In the field of medicine, there is a constant demand for new and improved biological markers (biomarkers) for diagnosing or prognosticating pathological conditions and for evaluating the efficacy of a treatment being applied. In general terms, the concentration of a biomarker from a patient sample is by statistical association taken as indication for the presence of, the severity of, or the risk for a pathological condition. One widely studied subset of biomarkers is peptides in biological fluids, such as blood, cerebrospinal fluid or urine. The number of different peptides present in the biological sample may vary from tens to tens of thousands, depending on the method of analysis and the type of sample. It is thus clear than many medically relevant peptide biomarkers are yet to be discovered.

A human protein named complement C3 is a well-studied component of the innate immune system, and substantial amounts of complement C3 circulate in the blood. The classical complement pathway typically requires antigen:antibody complexes for activation (specific immune response), whereas the alternative and mannose-binding lectin pathways can be activated by C3 hydrolysis or antigens without the presence of antibodies (non-specific immune response). In all three pathways, a C3-convertase cleaves and activates component C3, generating C3a and C3b, and causing a cascade of further cleavage and activation events.

A number of complement C3 peptide fragments useful as biomarkers are known in the literature. For instance, WO/2004/079371 discloses peptide fragments of complement C3 as markers useful in the diagnosis of autism. As another example, US20050048584A1 discloses a method for detecting Alzheimer's disease and differentiating Alzheimer's disease from other demential diseases using peptide biomarkers originating from complement C3.

Autism is a neuropsychiatric disorder with varying degrees of severity which affects around 2-5 in 1000 children worldwide and perhaps up to 1:110 in the US. The aetiology of autism is not understood but it is thought that both genetic and environmental factors contribute. Diagnosis for autism requires expert evaluation of the child's behaviour and given the enormous implications of a diagnosis to the child and the family, setting a firm diagnosis often takes significant time and effort. As such, a clinical assay based on objective measurements of biological variables for diagnosing autism is in great demand.

Treatment of autism includes behavioural training and management using positive reinforcement, self-help, and social skills training to improve behaviour and communication. Several different treatment suites have been developed, including Applied Behavioural Analysis (ABA), Treatment and Education of Autistic and Related Communication Handicapped Children (TEACCH), and sensory integration. Specialized therapies include speech, occupational, and physical therapy. There is no standard medical treatment for autism, but problematic behaviours and symptoms are sometimes treated with such pharmaceuticals such as antidepressants, antipsychotics, anticonvulsants and methylphenidate. However, no disease-modifying treatment exists.

CERTAIN OBJECTS OF THE INVENTION

Thus, it is an object of the present invention to provide a new biological marker useful in diagnosis. It is a further object of the invention to provide analytical methods for determining the concentration of the novel marker in samples e.g. biological samples e.g. for diagnostic purposes. Furthermore, it is an object of the invention to provide new and improved methods based on biological markers for diagnosing neurological and/or neuropsychiatric disorders, such as autism in particular, but also Asperger's syndrome, Alzheimer's disease, Parkinson's disease, amyotrophic lateral sclerosis, multiple sclerosis, schizophrenia, depression and bipolar disorder. A yet further object of the invention is to provide a treatment for autism that is disease-modifying and not merely symptomatic.

SUMMARY OF THE INVENTION

In a first aspect, the invention provides a peptide having the amino acid sequence $NH_2$—SSKITHRIHWESASLLR*—COOH (SEQ ID NO: 1), wherein the C-terminal residue denoted with R* has a side chain as depicted in Formula (I):

In a second aspect, a method for analysis, comprising the step of determining the presence, absence and/or concentration of a peptide according to the first aspect in a sample is provided. The sample is preferably a biological sample. More preferably, the biological sample is selected from the group consisting of: a blood sample, a plasma sample, heparinised plasma sample, EDTA-plasma sample, a serum sample, a urine sample, a saliva sample, a tear sample, a cerebrospinal fluid sample, an ascites sample, a tissue sample and a biopsy. Most preferably, the biological sample is a heparinised plasma sample.

The determination of presence, absence and/or concentration of the peptide may be performed by means of a method based on mass spectrometry such as MALDI-TOF, SELDI- TOF, LC-MS or LC-MS/MS; or by means of an immunochemical assay, such as ELISA, RIA, FIA or DELFIA.

In a third aspect, the invention provides an antibody specific to a peptide according to the first aspect. The antibody may be a monoclonal antibody or a polyclonal antibody.

In a fourth aspect, a product package for use in diagnostics, comprising a peptide according to the first aspect and/or an antibody according to the third aspect is provided. The product package may further comprise one or more of: protease inhibitors; instructions for determining the concentration of the peptide of the first aspect; a peptide of SEQ ID NO: 2; a peptide of SEQ ID NO: 3; an antibody specific to SEQ ID NO: 2; an antibody specific to SEQ ID NO: 3.

In a fifth aspect, a method of diagnosis for a neurological or neuropsychiatric disorder is provided, comprising the steps of:
  providing or obtaining a sample from the subject to be diagnosed;
  determining the concentration of a peptide of the first aspect in said sample; and
  comparing said concentration to a reference value based on the concentration of the peptide of the first aspect in a similar sample from a healthy control subject;
  wherein a lower concentration than the reference value in the sample is indicative of the presence of a neurological or neuropsychiatric disorder.

The method of the fifth aspect may further comprise the steps of
  determining the concentration of a peptide with sequence: SSKITHRIHWESASLLR (SEQ ID NO: 3) and/or SSKITHRIHWESASLL (SEQ ID NO: 2) in said sample; and
  comparing said concentration to a reference value based on the concentration of the same peptide(s) in a similar sample from a healthy control subject;
  wherein a higher concentration than the reference value in the sample is further indicative of the presence of a neurological or neuropsychiatric disorder.

In the method of the fifth aspect, the step of determining concentration may be performed by means of a method of the second aspect.

The neurological or neuropsychiatric disorder of the fifth aspect may be selected from autism, Asperger's syndrome, Alzheimer's disease, Parkinson's disease, amyotrophic lateral sclerosis, multiple sclerosis, schizophrenia, depression and bipolar disorder. Most preferably, the disorder is autism.

In a sixth aspect, use of a peptide according to the first aspect in a diagnostic method is provided. Preferably, the peptide is used in the diagnosis of autism, Asperger's syndrome, Alzheimer's disease, Parkinson's disease, amyotrophic lateral sclerosis, multiple sclerosis, schizophrenia, depression or bipolar disorder. Most preferably, the peptide is used in the diagnosis of autism.

In a seventh aspect, there is provided a method of diagnosis for autism, comprising the steps of:
  a. providing or obtaining a sample from the subject to be diagnosed;
  b. determining the level of activity of complement factor I in said sample; and
  c. comparing said activity to a reference value based on the level of activity of complement factor I in a similar sample from a healthy control subject;
  wherein a higher activity than the reference value in a sample is indicative of the presence of autism in the subject.

The sample in the method of the seventh aspect may be selected from the group consisting of: a blood sample, a plasma sample, heparinised plasma sample, EDTA-plasma sample, a serum sample, a urine sample, a saliva sample, a tear sample, a cerebrospinal fluid sample, an ascites sample, a tissue sample and a biopsy. Preferably, the sample is a plasma sample.

The method of the seventh aspect may further comprise performing the method of the fifth aspect for diagnosing autism, and aggregating the results to yield a more sensitive and/or selective diagnosis of autism.

The method of the fifth aspect for diagnosing autism may further comprise performing the method of the seventh aspect, and aggregating the results to yield a more sensitive and/or selective diagnosis of autism.

In an eighth aspect, there is provided a method of treatment for autism, comprising administering a complement factor I-inhibitor compound to a subject in need thereof.

In an ninth aspect, there is provided a use of a complement factor I-inhibitor compound for the manufacture of a medicament for the treatment of autism.

In a tenth aspect, there is provided a complement factor I-inhibitor compound for use in the treatment of autism.

The complement factor I-inhibitor compound of the eighth, ninth or tenth aspects may be selected from the group consisting of 6-amidino-2-naphthyl p-guanidinobenzoate dimethanesulfonate (FUT-175), serpin, a benzenesulfonyl fluoride such as Pefabloc® SC, suramin, a WAP-type inhibitor such as elastase-specific inhibitor (elafin). Preferably, the compound is selected from FUT-175, elafin and suramin.

In an eleventh aspect, there is provided a method for evaluating the efficacy of a treatment for autism in a subject, comprising the steps of:
  a. determining a baseline value for the level of the biomarker according to the first aspect in the subject prior to the treatment;
  b. administering the treatment to be evaluated to the subject;
  c. subsequent to (b), determining the level of the biomarker of the first aspect in the subject; and
  d. comparing the levels obtained in (a) and (c);
  wherein an increase in the level of biomarker according to the first aspect is indicative of a therapeutic response to the treatment.

In a twelfth aspect, there is provided a method for evaluating the efficacy of a treatment for autism in a subject, comprising the steps of:
  a. determining a baseline value for the level of complement factor I activity in the subject prior to the treatment;
  b. administering the treatment to be evaluated to the subject;
  c. subsequent to (b), determining the levels of complement factor I activity in the subject; and
  d. comparing the levels obtained in (a) and (c);
  wherein a decrease in the activity of complement factor I is indicative of a therapeutic response to the treatment.

The method of the eleventh aspect may further comprise performing the method of the twelfth aspect, and aggregating the results to yield improved sensitivity and/or selectivity.

The method of the twelfth aspect may further comprise performing the method of the eleventh aspect, and aggregating the results to yield improved sensitivity and/or selectivity.

DEFINITIONS

The terms autism and autism spectrum disorder (ASD) have the same meaning in the context of the present invention and refer to a diagnosis of autism according to the DSM-IV criteria (American Psychiatric Association Diagnostic and Statistical Manual of Mental Disorders).

The term sensitivity in the context of the present invention means the proportion of actual positive subjects who are correctly identified as such (e.g. the percentage of autistic subjects who are correctly identified as having the condition).

The term specificity in the context of the present invention means the proportion of actual negative subjects who are correctly identified as such (e.g. the percentage of healthy subjects who are correctly identified as not having autism).

Herein, biomarkers are on occasion identified using their observed approximate molecular weight as a name. Table II shows the relationships between observed molecular weight/name, sequence and SEQ ID NO.

DETAILED DESCRIPTION OF THE INVENTION

Novel Modified Peptide Biomarker

In a first aspect, the present invention discloses a modified peptide having the amino acid sequence $NH_2$—SSKITHRI-HWESASLLR*—COOH (SEQ ID NO: 1), wherein the side chain of the C-terminal residue denoted with R* is lacking the $NH_2$—C=NH moiety normally present in an arginine, whereby the side chain of the R* residue has the structure as depicted in Formula (I):

Figure 1:
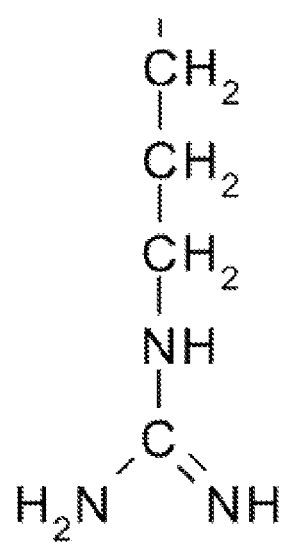
FIG. 1 illustrates the side chain modification of the C-terminal arginine in the novel peptide biomarker of SEQ ID NO: 1. A) Normal side chain of arginine. B) Structure of the modified side chain of the C-terminal arginine in the novel peptide biomarker of the invention. Such amino-acid with modified side chain is known as ornithine.
Figure 1:
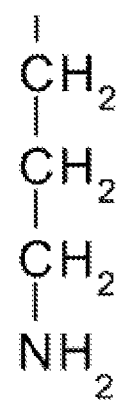

For additional illustration of the nature of the side chain modification, reference is made to FIG. 1. An amino-acid with the side chain of formula (I) is known as ornithine, but does not normally occur in polypeptides.

Methods of Analysis

In a second aspect, the present invention discloses a method for analysing the presence, absence and/or concentration of the peptide of the first aspect, preferably in a biological sample. The analysis may be performed by any means known in the art suitable for such analysis, such as methods based on mass spectrometry (including MALDI-TOF, SELDI-TOF, LC-MS, LC-MS/MS and the like) or suitable known immunochemical methods (including ELISA, RIA, DELFIA, and the like). It is also possible to combine immunochemical methods and methods based on mass spectrometry for the analysis, such as by using an antibody-coated chip in SELDI-TOF. In some cases, the sample may be concentrated or purified before the analysis. Concentration is especially preferable for dilute samples such as urine and cerebrospinal fluid. Such concentration and/or purification can e.g. be performed by using ultrafiltration (preferably with a suitable MW cut-off of about 1.0-1.5 kD if retention of the biomarker is desired; alternatively MW cut-off of about 10 kD can be used to remove proteins of higher molecular weight), by selective precipitation of proteins or by evaporating all or part of the fluid in the sample. Chromatographic techniques are also available for both concentrating the sample as well as for performing a purification. The binding characteristics to the CM10 surface at pH 7 (Example 3) provide a suitable starting point for optimising a chromatographic purification scheme.

Preferably, the biological sample is selected from: a blood sample, a plasma sample, heparin-treated plasma sample, EDTA-plasma sample, a serum sample, a urine sample, a saliva sample, a tear sample, a cerebrospinal fluid sample, an ascites sample, a tissue sample and a biopsy. More preferably, the biological sample is a heparin plasma sample. Most preferably, the biological sample is a heparin plasma sample treated with protease inhibitors, such as EDTA-Free inhibitor cocktail (Halt protease inhibitor from Thermo Scientific, USA) (e.g. 10 µL/mL plasma) and Pefablock® SC (Pentapharm Ltd Switzerland) (e.g. 20 µL/mL plasma).

Antibodies

In a third aspect, the present invention relates to an antibody specific for the peptide of the first aspect. Aided with the disclosure of the peptide itself presented herein, the skilled person will be able to apply methods well known in the art to obtain and characterize specific polyclonal or monoclonal antibodies to the peptide.

Diagnostic Products

In a fourth aspect, a diagnostic product (such as a kit) is disclosed, comprising a peptide of the first aspect and/or an antibody of the third aspect. Preferably, the diagnostic product further comprises one or more of: directions for use; protease inhibitors; a peptide of SEQ ID NO: 2; a peptide of SEQ ID NO: 3; an antibody specific to SEQ ID NO: 2; an antibody specific to SEQ ID NO: 3. The peptides may serve as positive controls/reference samples and the antibodies may serve as detection reagents for use in an immunological method of analysis.

Diagnostic Methods

In a fifth aspect, a diagnostic method for neurological and/or neuropsychiatric disorder is disclosed, based on determining the peptide marker of the first aspect, preferably by means of a method of the second aspect. The peptide marker of SEQ ID NO: 1 can advantageously be combined with determination of known diagnostic markers, such as those disclosed in WO/2004/079371 (preferably SEQ ID NO: 2 and SEQ ID NO: 3). Combining the results from the peptide marker of the first aspect with additional markers provides a diagnostic method with improved specificity and/or sensitivity.

In order to be diagnostically useful, the concentrations of the above marker or markers must be compared to a reference value (also known as a "cut-off"). Suitably, the reference value is obtained by determining the concentrations of the same markers (most preferably using similar methods and similar samples) from a healthy control subject or more preferably by obtaining an average value from a group of healthy control subjects. The marker of the first aspect is found in healthy subjects but tends to be absent or to have a lower concentration in subjects with a neurological and/or neuropsychiatric disorder, such as autism.

Figure 4:
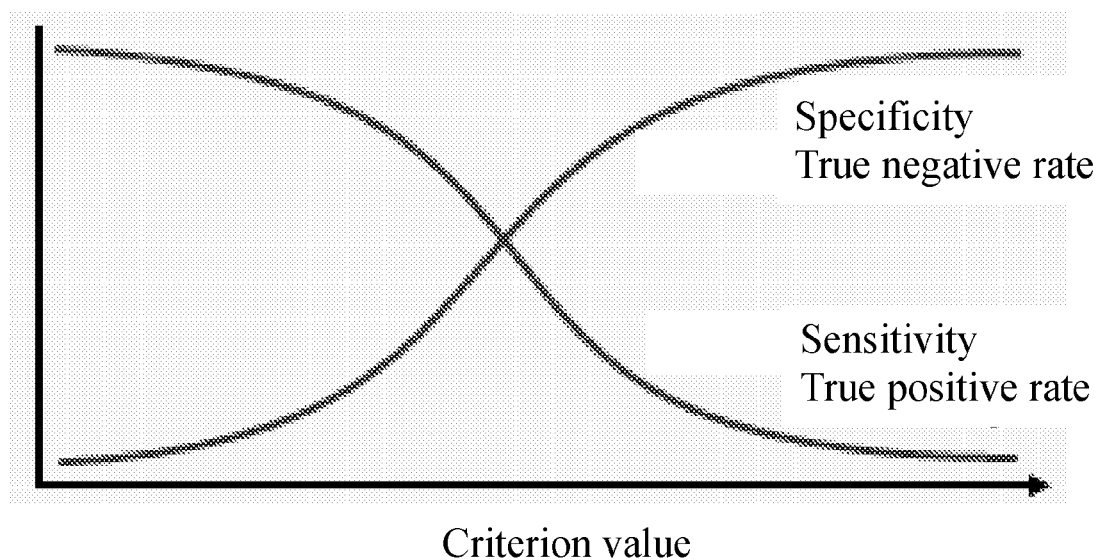
FIG. 4 illustrates the reciprocal relation that exists between a cut-off criterion, selectivity and sensitivity.

The skilled person will appreciate that the level of difference from the reference value that is taken as indicative of presence of a disorder will vary from case to case, as in most real-world cases the marker concentrations in the healthy population and in the population with a disorder will partially overlap to a degree. Requiring larger difference will increase the specificity of the diagnostic method but sacrifices sensitivity; requiring smaller difference will increase sensitivity at the cost of decreased specificity (see FIG. 4 for illustration). The desirable levels of specificity and sensitivity will vary depending on the setting: for example, in a screening procedure testing subjects without prior suspicion of a disorder a very high specificity is necessary to avoid large numbers of false positives; when testing subjects already suspected of having a disorder, a high sensitivity may be prioritized instead and lower specificity accepted. The determined concentration (s) of the marker or markers are also likely to vary depending on characteristics of the particular analytical method used to assay the concentrations as well as the type of sample and handling of the sample. All these considerations are well known to the skilled person. Likewise, solutions to the issues presented above (e.g. determining the cut-off values) are within the reach of the skilled person by combining the teachings herein with mere routine experimentation and optimisation.

A statistical tool useful in determining the cut-off values is known as Receiver Operating Characteristic (ROC) curve, which may be constructed as follows. Rank all subjects (patients plus controls) after the measured parameter. Start from the upper part of the table and calculate, successively for each new measured value, the sensitivity and 100-specificity for all subjects (sensitivity=posP/allP, where posP is the number patients (patients meaning the subjects with the disease) that would be classified as having the disease using this measured value and specificity is negC/allC, where negC is the controls that are not classified having the disease). Plot these values in an x-y-diagram where "100-specificity is x" and sensitivity is y, resulting in a ROC-curve.

The cut-offs are always adjusted to the actual situation including prevalence of the disease and especially the degree of severity of the disease but statistical programs (knowing nothing about the clinical situation) usually calculate the cut-offs by minimizing the distance from the upper left corner of the ROC-curve, i.e. minimizing ((100-sensitivity)^2+(100-specificity)^2), where ^ means squared (Pythagoras theorem). The values of "Criterion" (meaning cut-off), sensitivity and selectivity shown in FIGS. 5-8 were obtained by using this method.

With regard to combinations of biomarkers it is important to sort out which actually are independent in the sense that they contribute to the discrimination of patients and controls (at least to some extent—that means e.g. that a peak, although coupled to another peak, has something extra to contribute to the discriminating power). A number of known statistical methods can be used, e.g. discriminant analyses or logistic regression. For additional details, the skilled reader is referred to the manual of MedCalc® software (MedCalc Software, Mariakerke, Belgium) available online at: http://www.medcalc.oremanual/index.php.

Figure 3:
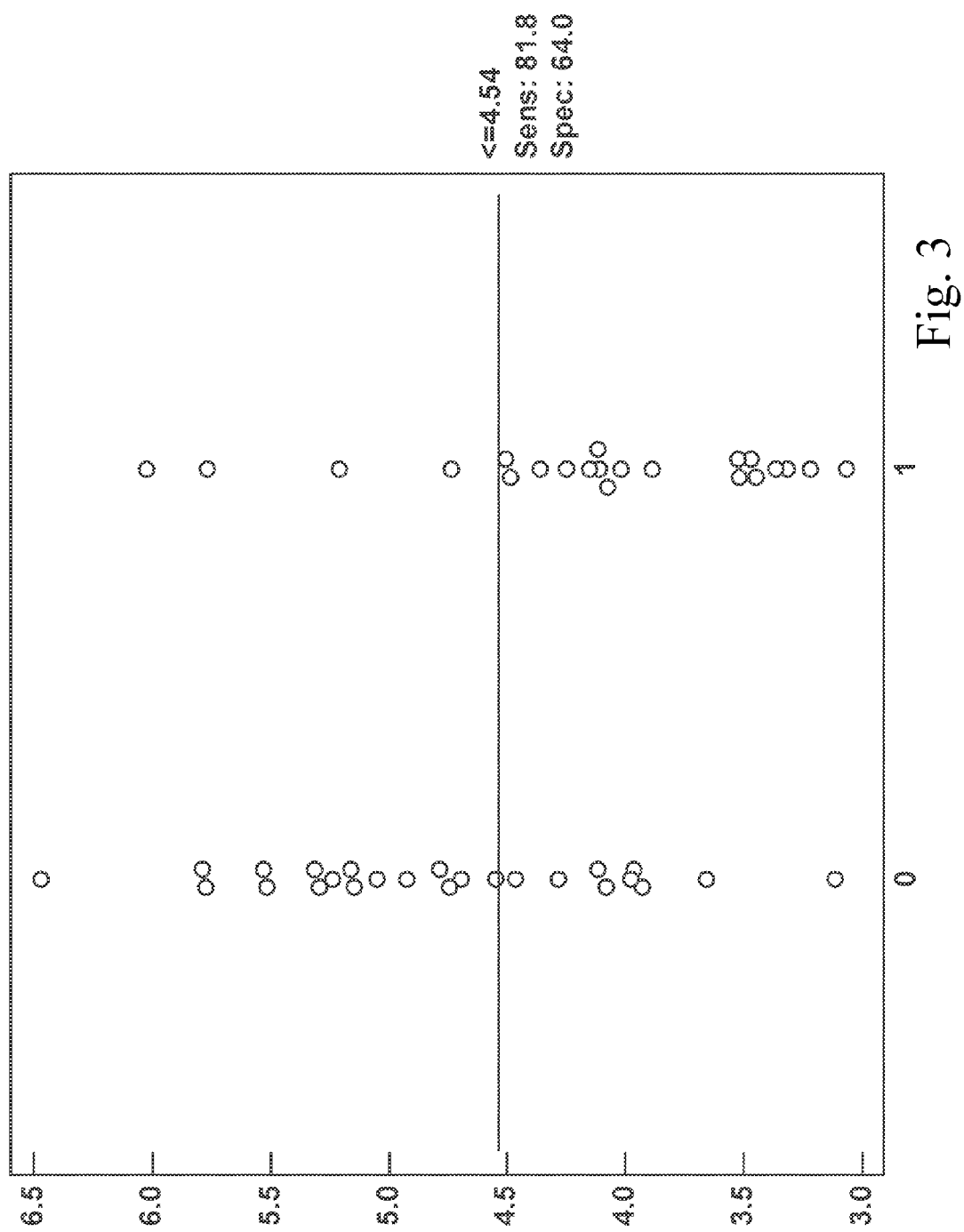
FIG. 3 shows the measurements of Example 3 for the marker 1978 (SEQ ID NO: 1) (values in Table I) in graph form. The group denoted "0" contains results from healthy control subjects, whereas the group denoted "1" contains results from autistic subjects.
Figure 6:
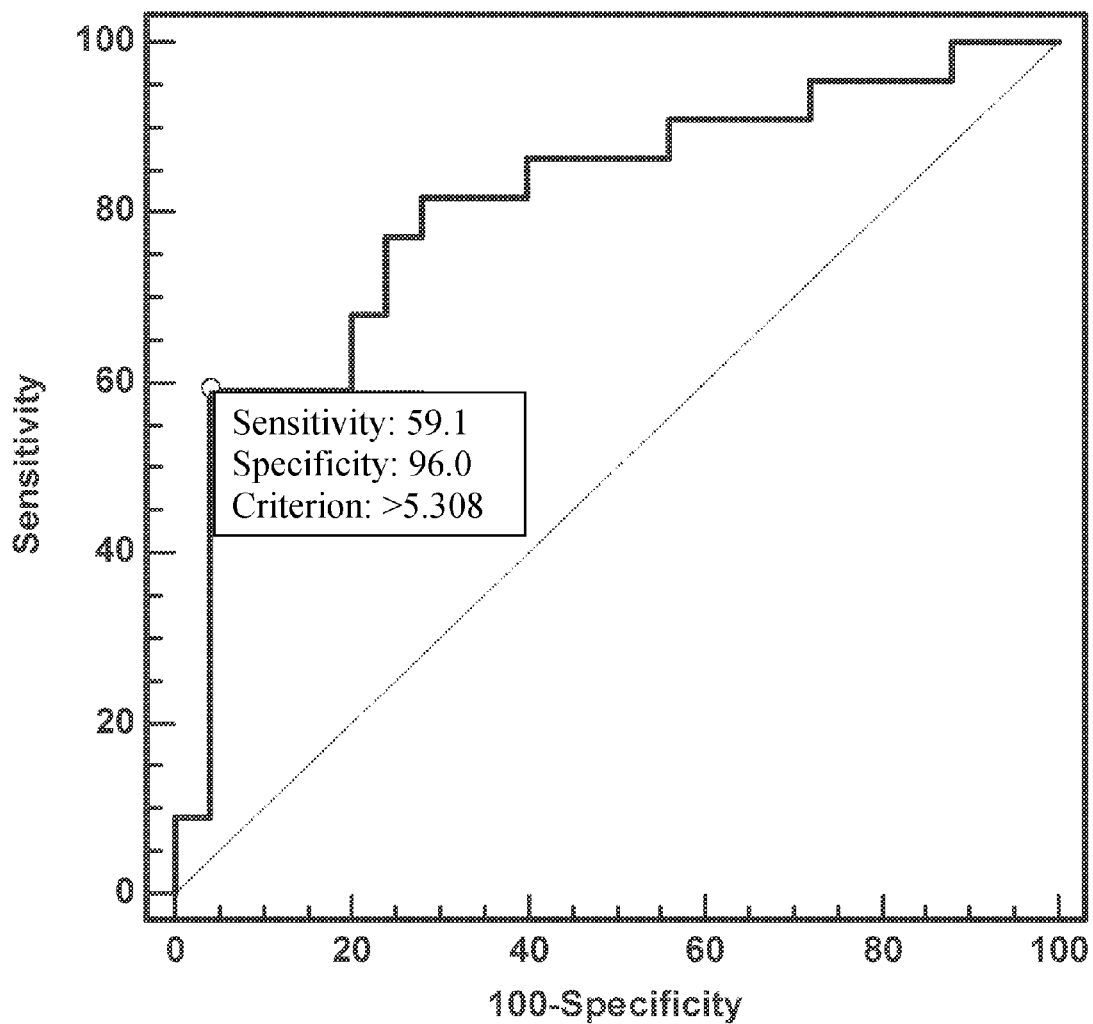
FIG. 6 is a comparative example depicting a receiver operating characteristic (ROC) curve of the known peptide biomarker of SEQ ID NO: 3 in diagnosis of autism based on data from Example 3.
Figure 7:
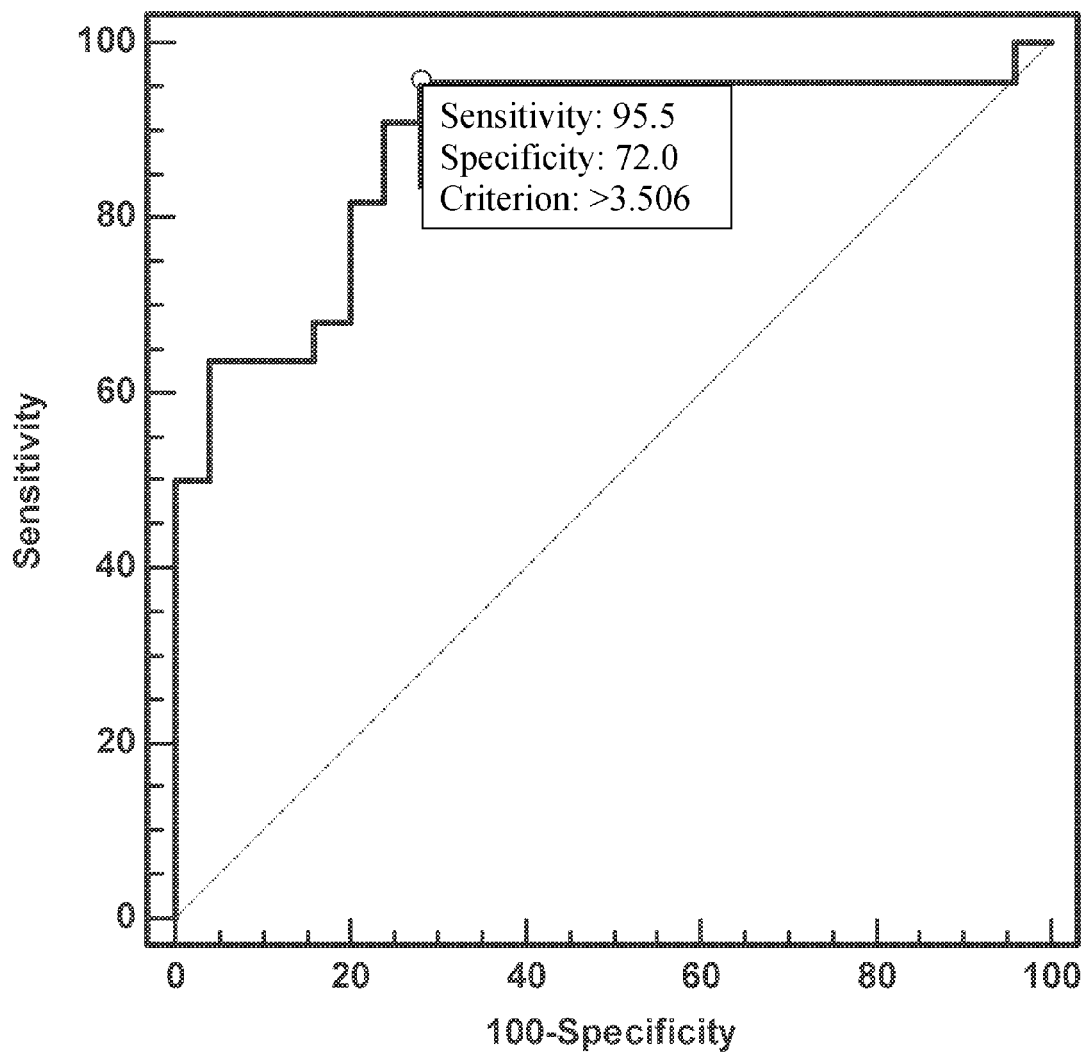
FIG. 7 depicts a receiver operating characteristic (ROC) curve obtained by combining the novel peptide biomarker of SEQ ID NO: 1 with the known marker of SEQ ID NO: 3 for diagnosing autism based on data from Example 3. Improved sensitivity and selectivity are apparent compared to either marker in isolation.
Figure 8:
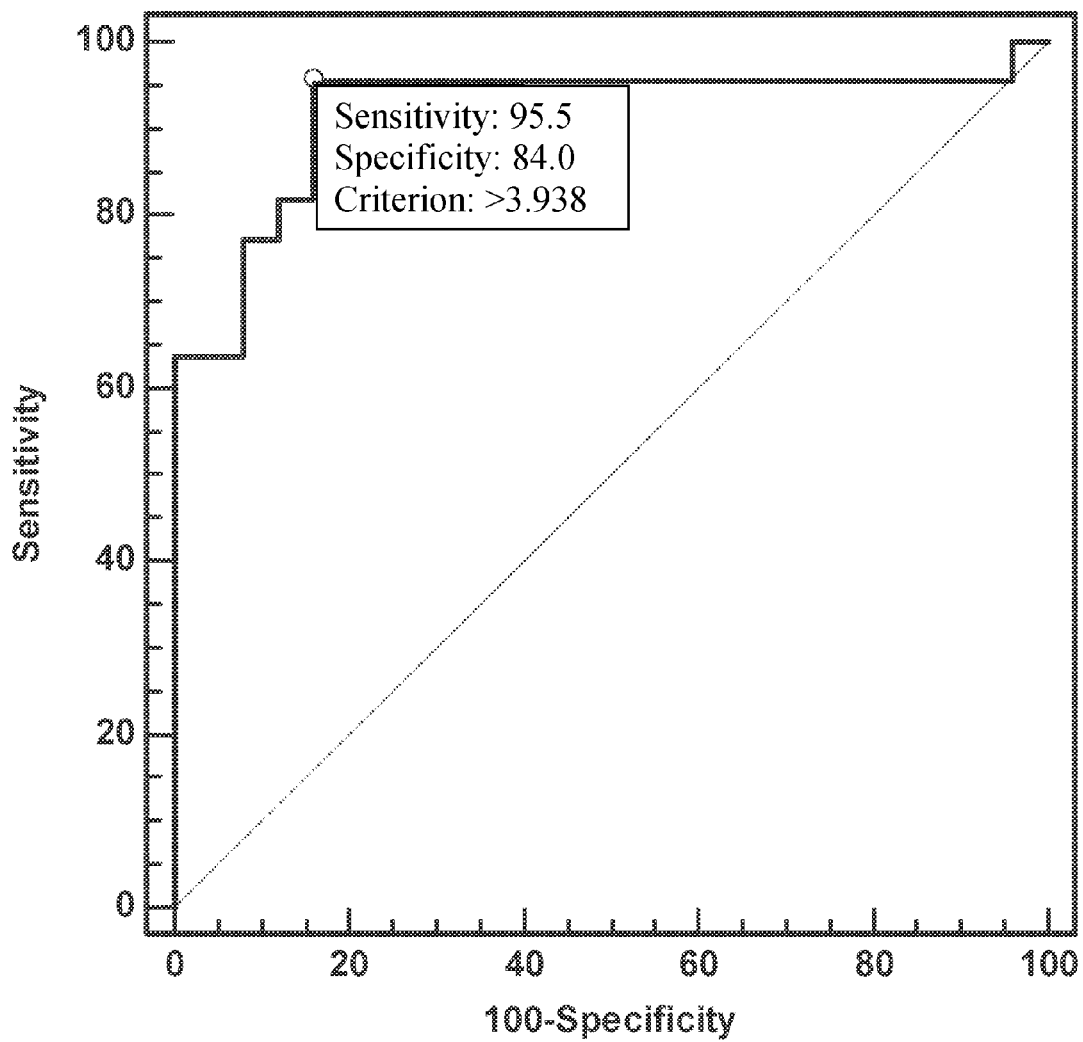
FIG. 8 depicts a receiver operating characteristic (ROC) curve obtained by combining the novel peptide biomarker of SEQ ID NO: 1 with the known markers of SED IQ NO: 2 and SEQ ID NO: 3 for diagnosing autism based on data from Example 3. Improved sensitivity is apparent.

Considering the above, an exemplary analysis was undertaken (Example 5). The analysis showed that the novel 1978 marker (SEQ ID NO: 1) clearly had considerable potential in differentiating subjects with and without autism having discriminative power on par with the known markers 2021 (SEQ ID NO: 3) and 1865 (SEQ ID NO: 2) (Table III, FIGS. 3, 5 and 6). In order to test the hypothesis that combining the novel 1978 marker with one or both of known markers 1865 and 2021 would result in an improved diagnostic method, ROC curves were also devised (after discriminant analysis) for the combination of 1978 with 2021 (FIG. 7) and the combination of 1865, 1978 and 2021 (FIG. 8). It is apparent from comparison of the ROC-curve of FIG. 7 to the curves of FIG. 5 and FIG. 6 that combining the novel 1978 marker with the known 2021 marker yields better results than either marker in isolation. Addition of the second known marker 1865 to the analysis gives yet better results (FIG. 8 in comparison to FIG. 7).

Preferably, the neurological or neuropsychiatric disease to be diagnosed is selected from autism, Asperger's syndrome, Alzheimer's disease, Parkinson's disease, amyotrophic lateral sclerosis, multiple sclerosis, schizophrenia, depression and bipolar disorder. Most preferably the neurological or neuropsychiatric disease to be diagnosed is autism.

In a seventh aspect, there is provided a method of diagnosis for autism, comprising the steps of:
a. providing or obtaining a sample from the subject to be diagnosed;
b. determining the level of activity of complement factor I in said sample; and
c. comparing said activity to a reference value based on the level of activity of complement factor I in a similar sample from a healthy control subject;
wherein a higher activity than the reference value in a sample is indicative of the presence of autism in the subject.

The sample in the method of the seventh aspect may be selected from the group consisting of: a blood sample, a plasma sample, heparinised plasma sample, EDTA-plasma sample, a serum sample, a urine sample, a saliva sample, a tear sample, a cerebrospinal fluid sample, an ascites sample, a tissue sample and a biopsy. Preferably, the sample is a plasma sample.

The determination of the level of activity of complement factor I may be performed using a fluorogenic assay as described in Example 6 (see section 6.1.2.2). Other methods for determining may naturally also be used.

The reference value for complement factor I may be obtained as disclosed above, mutatis mutandis.

The method of the seventh aspect may further comprise performing the method of the fifth aspect for diagnosing autism, and aggregating the results to yield a more sensitive and/or selective diagnosis of autism. The aggregation may be performed e.g. using the ROC method described above where the complement factor I-activity is taken as a determinant.

The method of the fifth aspect for diagnosing autism may further comprise performing the method of the seventh aspect, and aggregating the results to yield a more sensitive and/or selective diagnosis of autism.

The present invention also discloses the use of a peptide of the first aspect in a diagnostic method, preferably a method for diagnosing autism.

Treatment of Autism

Momeni et al. have disclosed (Autism Research and Treatment Volume 2012 (2012), Article ID 868576, doi:10.1155/2012/868576) that children with autism spectrum disorders have high complement factor I activity in plasma (Example 6).

Complement factor I is a serine protease present in human plasma that is involved in the degradation of complement protein C3b. Deficiency in complement factor I activity is associated with an increased incidence of infections in humans.

In said paper, Momeni et al. show that the mean level of complement factor I activity in the ASD group is significantly higher than in the control group of typically developed and healthy children, suggesting that high activity of complement factor I might have an impact on the development of ASD.

Thus, there is provided a treatment for autism using an inhibitor for complement factor I. A number of complement factor I-inhibitor compounds and classes of compounds are known, including 6-amidino-2-naphthyl p-guanidinobenzoate dimethanesulfonate (FUT-175), serpin, benzenesulfonyl fluorides such as Pefabloc® SC, suramin, WAP-type inhibitors such as elastase-specific inhibitor (elafin) (Example 7).

Establishing the appropriate dosing of the complement factor I-inhibitor can be performed by a person skilled in the art by way of mere routine experimentation and optimization. In cases of known compounds where a safe dose interval for use in humans is known, the natural starting point for experimentation is said interval. The efficacy of treatment (improvement of function) can be followed compared to baseline (i.e. before the initiation of treatment) by repeated (e.g. weekly) assessments under the paradigm described in the Examples under 6.1.1.

FUT-175 may be administered orally. The dosing may be initiated with 0.1 mg/kg/day (divided in two daily doses), and where necessary increased to 0.25 mg/kg/day (divided in two or four daily doses) and subsequently to 0.5 mg/kg/day (divided in four daily doses).

Suramin may be administered by intravenous injection, starting with 0.1 g per single weekly intravenous injection. Where necessary, the dose is escalated in increments of 0.1 g to up to 1 g per injection.

Elafin may be administered by intravenous injection, starting with 10 mg twice daily. Where necessary, the dose is escalated to 20, 100, 200 and then 400 mg per injection.

Methods for Evaluating the Efficacy of a Treatment for Autism

In an eleventh aspect, there is provided a method for evaluating the efficacy of a treatment for autism in a subject, comprising the steps of:
a. determining a baseline value for the level of biomarker according to the first aspect in the subject prior to the treatment;
b. administering the treatment to be evaluated to the subject;
c. subsequent to (b), determining the level of the biomarker of the first aspect in the subject; and
d. comparing the levels determined in (a) and (c);
wherein an increase in the level of the biomarker according to the first aspect is indicative of a therapeutic response to the treatment.

The determination of the values can be performed in the manner disclosed for the fifth aspect.

In a twelfth aspect, there is provided a method for evaluating the efficacy of a treatment for autism in a subject, comprising the steps of:
a. determining a baseline value for the level of complement factor I activity in the subject prior to the treatment;
b. administering the treatment to be evaluated to the subject;
c. subsequent to (b), determining the level of complement factor I activity in the subject; and
d. comparing the levels determined in (a) and (c);
wherein a decrease in the activity of complement factor I is indicative of a therapeutic response to the treatment.

The determination of the values can be performed in the manner disclosed for the seventh aspect.

The method of the eleventh aspect may further comprise performing the method of the twelfth aspect, and aggregating the results to yield improved sensitivity and/or selectivity.

The method of the twelfth aspect may further comprise performing the method of the eleventh aspect, and aggregating the results to yield improved sensitivity and/or selectivity.

Concluding Remarks

The following examples are to be seen as non-limiting. The references used herein are hereby incorporated by reference in their entirety.

EXAMPLES

1. Patient and Control Selection

All children with autism spectrum disorder (ASD) were examined by clinical experts on autism. A child psychiatrist examined all the children who were also examined by a child neurologist or a child psychologist. All consultants agreed on the diagnosis of autism according to the DSM-IV criteria (American Psychiatric Association Diagnostic and Statistical Manual of Mental Disorders). The control group consisted of healthy children with no signs of neurological and/or neuropsychiatric disorders recruited from the same area. Control children who had any kind of infection disease prior two weeks ago at the time of examination were excluded from this study.

There were no significant differences in age and gender. Children in the ASD group were recruited from the autism rehabilitation centre.

2. Sampling

Venous blood was collected into 3 mL Heparine tubes (Vacutainer System; Becton-Dickinson Inc., Plymouth, UK) and plasma was separated immediately by centrifugation at 1300 g for 10 min at 4° C. Thereafter, an EDTA-Free inhibitor cocktail (Halt protease inhibitor from Thermo Scientific, USA) (10 µL/mL plasma) and additional 20 µL/mL of Pefablock SC (Pentapharm Ltd Switzerland) was added to the produced plasma sample. The produced plasma was aliquoted into small portions and immediately frozen on dry ice and thereafter transported to (−80° C.) for further storage. The entire procedure from blood collection to freezing was completed within 20 minutes.

3. Mass-spectrometric Analysis (SELDI-TOF)

CM10 protein chip array surfaces were prepared according to the Standard protocol from BioRad. CM10 protein-chip arrays (bearing COOH functional group) with 8 spots were equilibrated by 100 µL buffer (low-stringency 0.1 M Na acetate, pH 4) for 5 min and repeated once. Na phosphate buffer (25 mM, pH-7.0) was used to prepare plasma dilutions (1:50 dilution). The diluted plasma was applied on the bioprocessor well. The chip array was incubated for 45 min with vigorous shaking. After incubation the samples were washed three times with 150 µL of 25 mM Na phosphate buffer pH-7 (the same as dilution buffer), followed by two quick rinses with 150 µL of 1 mM HEPES (N-2-Hydroxyethylpiperazine-N'-2-Ethanesulfonic Acid), pH 7. The chip array was removed from bioprocessor and was air dried. Later, 0.8 µL of saturated CHCA (25 mg/mL) was added to each spot and allowed to air-dry and this step was repeated 1 more times. Thereafter chip arrays were read by BioRad protein cheap reader SELDI system personal Edition (PCS 4000 reader). Prior to reading the chip arrays, an external calibration was done by using Biorad "all in one peptide standard" which is a mixture of 7 different peptides ranging from about 1000-7000 Da.

In the study, samples from 22 controls and 25 patients were analysed by SELDI-TOF as specified above. The measured data was normalized by natural logarithms (Table I, FIG. 3).

Figure 2:
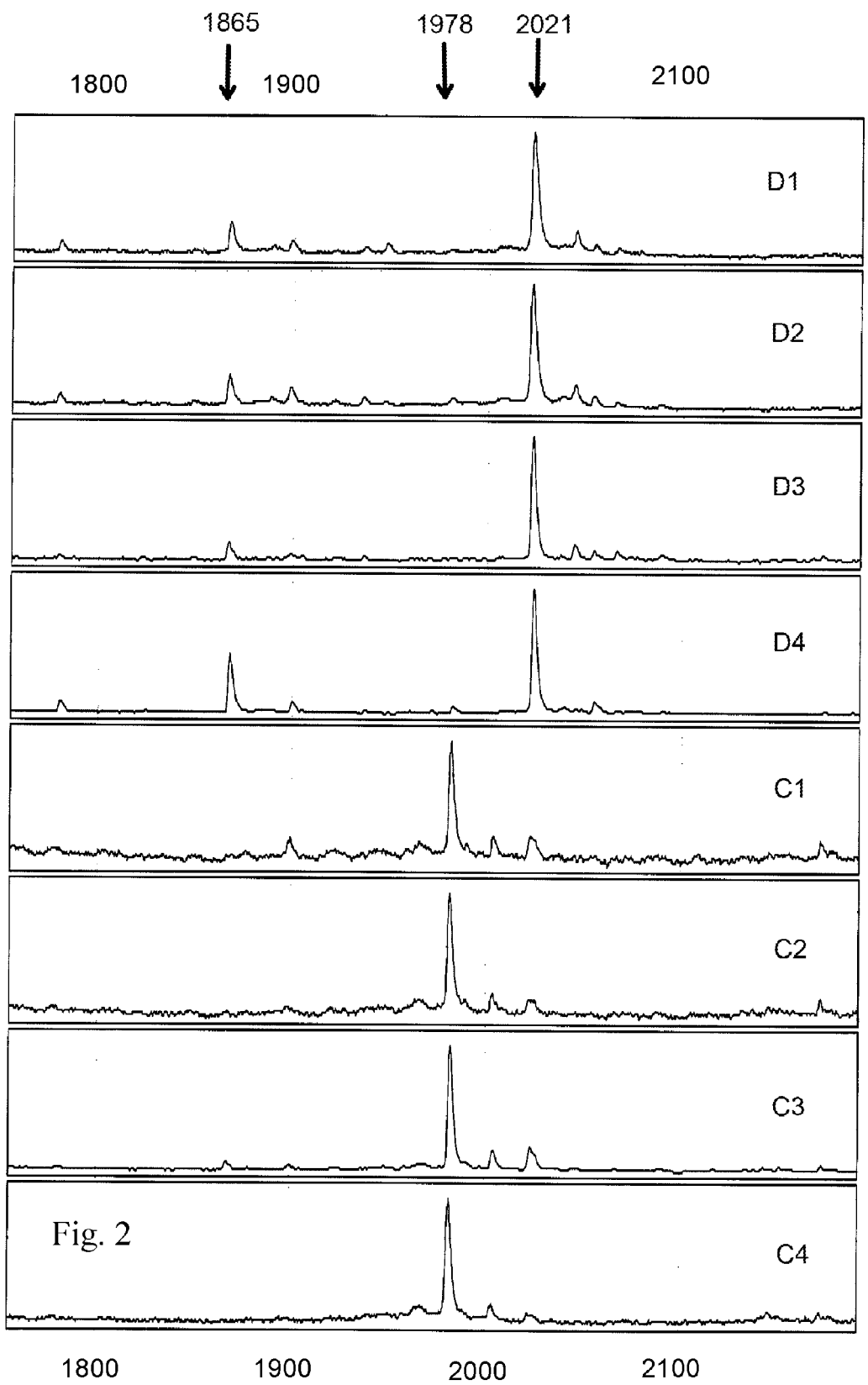
FIG. 2 shows representative mass spectra from samples derived from 4 different subjects with diagnosis of autism (denoted D) and 4 different subjects of healthy control children (denoted C). The positions markers of 1865 (SEQ ID NO: 2), 1978 (SEQ ID NO: 1) and 2021 (SEQ ID NO: 3) are indicated at the top. It is apparent that the markers 1865 and 2021 are elevated in subjects with autism, whereas the marker 1978 is reduced in autistic subjects compared to in healthy subjects. Y-axis units: µA. X-axis: apparent MW (Daltons). Y-axis was scaled automatically to reveal the relevant peak. Y-axis approximate scales for each panel are as follows: D1: 0-700; D2: 0-1000; D3: 0-350; D4: 0-800; C1: 0-300; C2: 0-400; C3: 0-650; C4:0-650.

A number of differentially expressed peptides such has having observed molecular weights of 1865, 1978 and 2021 in the spectra from healthy control children and ASD group were detected. Representative SELDI-TOF spectra from 8 subjects (4 different patients and 4 different controls) are shown in FIG. 2.

TABLE I

Normalized (natural logarithm) peak intensities for markers having molecular weights (MWs) of approximately 1865, 1978 and 2021, respectively

| Group | ID | 1865 | 1978 | 2021 |
|---|---|---|---|---|
| Controls | c1 | 2.451 | 5.237 | 4.61 |
| Controls | c10 | 2.397 | 5.146 | 5.06 |
| Controls | c11 | 3.231 | 3.972 | 5.19 |
| Controls | c12 | 3.33 | 3.963 | 5.136 |
| Controls | c13 | 3.436 | 5.154 | 4.256 |
| Controls | c17 | 3.426 | 5.781 | 3.847 |
| Controls | C18 | 3.415 | 5.046 | 5.206 |
| Controls | c2 | 3.827 | 4.28 | 4.592 |
| Controls | c20 | 3.633 | 5.287 | 5.308 |
| Controls | c21 | 3.105 | 4.689 | 4.733 |
| Controls | c22 | 2.819 | 4.782 | 4.355 |
| Controls | c23 | 5.327 | 6.463 | 6.723 |
| Controls | c24 | 2.549 | 5.526 | 4.516 |
| Controls | c25 | 3.476 | 5.307 | 4.292 |
| Controls | c26 | 3.543 | 4.542 | 4.207 |
| Controls | c28 | 3.041 | 5.766 | 4.708 |
| Controls | c29 | 2.801 | 4.116 | 4.52 |
| Controls | c3 | 2.734 | 4.464 | 5.199 |
| Controls | c31 | 2.978 | 3.653 | 4.454 |
| Controls | c33 | 2.567 | 5.514 | 4.739 |
| Controls | c4 | 3.908 | 4.742 | 5.003 |
| Controls | c6 | 3.519 | 4.917 | 4.976 |
| Controls | c7 | 2.361 | 3.925 | 5.039 |
| Controls | c8 | 2.508 | 3.112 | 5.038 |
| Controls | c9 | 2.628 | 4.078 | 4.358 |
| Patients | d10 | 4.253 | 4.504 | 6.548 |
| Patients | d11 | 3.534 | 5.209 | 7.229 |
| Patients | d13 | 6.522 | 4.731 | 5.353 |
| Patients | d14 | 5.462 | 4.483 | 6.577 |
| Patients | d15 | 3.427 | 4.244 | 5.13 |
| Patients | d17 | 3.934 | 4.358 | 5.135 |
| Patients | d19 | 3.811 | 3.522 | 5.055 |
| Patients | d20 | 1.937 | 3.214 | 5.328 |
| Patients | d21 | 3.616 | 3.517 | 6.03 |
| Patients | d22 | 3.623 | 3.883 | 5.791 |
| Patients | d25 | 3.229 | 3.064 | 6.077 |
| Patients | d26 | 3.497 | 3.467 | 4.5 |
| Patients | d27 | 3.288 | 4.105 | 5.311 |
| Patients | d28 | 2.662 | 3.312 | 5.547 |
| Patients | D3 | 5.297 | 5.76 | 6.936 |
| Patients | d30 | 3.379 | 6.022 | 4.273 |
| Patients | d4 | 3.311 | 4.072 | 4.987 |
| Patients | D5 | 3.745 | 4.116 | 5.153 |
| Patients | D6 | 4.652 | 4.146 | 4.651 |
| Patients | d7 | 5.667 | 4.016 | 6.23 |
| Patients | d8 | 3.528 | 3.448 | 6.404 |
| Patients | d9 | 3.559 | 3.362 | 5.15 |

4. Determination of Structures of Differentially Expressed Biomarkers

The structure of the differentially expressed biomarkers in Example 3 were determined by using MALDI-TOFTOF MS and confirmed by LC-FTICR MS/MS information. Peptide of interest (those which was identified by SELDI-TOF and significantly differed between control and autism group) were identified and sequenced.

100 µL of plasma samples was diluted with 300 µL buffer (25 mM Na-phosphate buffer, pH 7.0) and 100 µL Acetonitrile (AcN) and mixed well, thereafter an ultrafiltration was performed by use of a 10 kDa cut-off Microcon membrane (Millipore Bedford, Mass., USA). The ultrafiltrate was dried in a Speed vac centrifuge and thereafter reconstituted in 10 µL of buffer (25 mM Na-phosphate, pH 7.0), desalted on a Zip-Tip® $C_{18}$ column (Millipore, Bedford, Mass., USA). 5 µL of the reconstituted sample was applied on the prepared SELDI-TOF CM-10 target (Biorad, USA), incubated, washed and dried.

1.0 µL of saturated Matrix CHCA (25 mg/mL) was added to the sample spots and allowed to air-dry and this step was repeated 1 more time.

The MALDI-TOF-MS instrument used for the verification of the peptides was an Ultraflex II TOF/TOF (Bruker Daltonik GmbH, Bremen, Germany) The instrument was equipped with a SmartBeam™ laser. All spectra were acquired using the reflectron mode. In order to acquire MS/MS spectra, post source decay (PSD) TOF/TOF by laser-induced dissociation was performed.

The target of choice for the MALDI approach was the SELDI-TOF target (BioRad, USA). The prepared matrix/sample spots on the SELDI-TOF target were introduced into the Ultraflex II and MS spectra were recorded from prepared sample spot. The calibration used was an external near neighbor calibration. The samples used for calibration were a mixture of peptides covering the mass range from 1000 to 5000 Da. From the acquired peptide masses (TOF MS data), the candidate peptide were selected manually for subsequent experiments/sequencing. Spectra were annotated with data processing software (FlexAnalysis™) and finally interpreted by software assisted de novo sequence analysis (BioTools™). Results for differentially expressed peptides are shown in Table II below.

TABLE II

Structure determination of differentially expressed peptides

| Observed MW/name | Amino-acid sequence | SEQ ID NO: |
|---|---|---|
| 1978 | SSKITHRIHWESASLLR* | 1 |
| 1865 | SSKITHRIHWESASLL | 2 |
| 2021 | SSKITHRIHWESASLLR | 3 |

*denotes modified C-terminal arginine: $NH_2-C=NH$ moiety is lost from side chain (see also FIG. 1)

5. Diagnostic Value of the Differentially Expressed Biomarkers

A statistical analysis of the results obtained in Example 3 (Table I) was performed using computer programs such as MedCalc® software (MedCalc Software, Mariakerke, Belgium).

All the markers showed statistically significant differences ($p<0.05$) between the control group and the autistic group (two-sided t-test). See table III.

TABLE III

Statistical analysis of data shown in Table II.

| Marker | Mean Autistic | Mean Controls | t-value | df | p | t separ. var. est. | df | p 2-sided | Std. Dev. Patients | Std. Dev. Controls |
|---|---|---|---|---|---|---|---|---|---|---|
| 2021 | 5.608718 | 4.802606 | 4.05927 | 45 | 0.000194 | 3.96775 | 36.806 | 0.000323 | 0.798449 | 0.554487 |
| 1865 | 3.906028 | 3.160416 | 2.97598 | 45 | 0.004686 | 2.8918 | 34.333 | 0.006603 | 1.043658 | 0.65134 |
| 1978 | 4.116157 | 4.778406 | −2.89728 | 45 | 0.005795 | −2.89437 | 44.059 | 0.005888 | 0.788326 | 0.776276 |

The novel 1978 marker clearly showed considerable potential in differentiating subjects with and without autism having discriminative power in par with the known markers 2021 and 1865.

Figure 5:
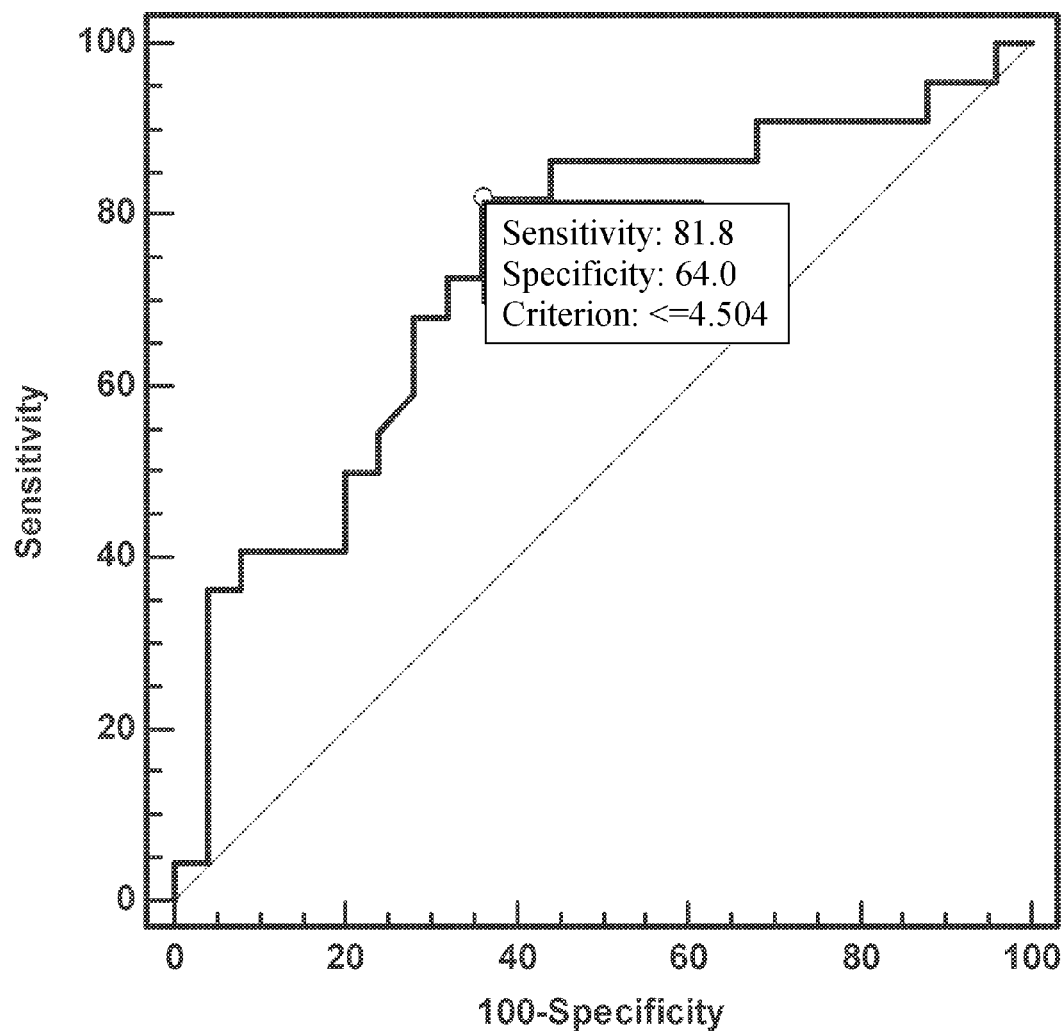
FIG. 5 depicts a receiver operating characteristic (ROC) curve of the novel peptide biomarker of the invention (SEQ ID NO: 1) in diagnosis of autism based on data from Example 3.

For the 1978 marker, a receiver operating characteristic (ROC) curve was devised (FIG. 5). For comparative purposes a ROC curve was also devised for the known 2021 marker (FIG. 6).

For analysing the utility of combining of the biomarkers above, discriminant analyses was used giving the peaks (logarithmic values) different weights according to their contribution to the discrimination which prospectively can be used clinically to diagnose the disease.

TABLE IV

Discriminant analysis of marker combinations for ROC-curve construction

| Combination of markers | Weighing based on discriminant analysis | Resulting ROC-curve |
|---|---|---|
| 1865 and 1978 | 1865 * (1.73) + 1978 * (−1.87) | Not shown |
| 1865 and 2021 | 2021 * (1.48) + 1865 * (0.62) | Not shown |
| 1978 and 2021 | 2021 * (1.99) + 1978 * (−1.36) | FIG. 7 |
| 1865, 1978 and 2021 | 2021 * (1.52) + 1978 * (−1.90) + 1865 * (1.33) | FIG. 8 |

ROC-curves of FIGS. 7 and 8 clearly indicate that combinations of the novel marker 1978 with known markers results in improved discriminative power.

6. Complement Factor I is Overactive in Autistic Patients

This study was published earlier by Momeni et al. (Autism Research and Treatment Volume 2012 (2012), Article ID 868576, doi:10.1155/2012/868576). Said publication is hereby incorporated by reference in its entirety. Certain key sections are reproduced below.

6.1 Materials and Methods
6.1.1 Participants

Thirty children with ASD and thirty typical control children participated in this study. The ASD group comprised 23 boys and 7 girls with a mean age of 4.5 years (age range 3-9 years). The control group comprised 13 boys and 17 girls, mean age 6.0 years (age range 3-12 years), (Table V).

TABLE V

Age/y, gender, and medication of the participants.

| Parameter | | ASD (n = 30) | Controls (n = 30) | P value* |
|---|---|---|---|---|
| Age | Mean (SD) | 4.8 (1.7) | 6.1 (2.3) | |
| | Median (range) | 4.5 (3-9) | 6 (3-12) | 0.033 |
| | ≤5 years | 21 | 14 | |
| | >5 years | 9 | 16 | 0.115 |
| Gender | Males | 23 | 13 | |
| | Females | 7 | 17 | 0.017 |
| Medication | No specific medication | 8 | 30 | — |

TABLE V-continued

Age/y, gender, and medication of the participants.

| Parameter | | ASD (n = 30) | Controls (n = 30) | P value* |
|---|---|---|---|---|
| | Risperdal alone or in combination | 18 | 0 | — |
| | Ritalin or in combination | 4 | 0 | — |

*Difference between ASD and controls. Mann-Whitney U-test for age and Fisher's exact test for age category and gender.

Children in the ASD group were recruited from the Autism Rehabilitation Centre at the University of Social Welfare and Rehabilitation Sciences in Tehran, Iran. After having obtained informed consent from the parents, blood samples were collected. All children with ASD were examined by clinical specialists on autism. A child psychiatrist and a child neurologist or child psychologist examined all of the children. All consultants agreed on the diagnosis of autism according to the DSM-IV criteria. However, diagnostic procedures applied in Europe and in the US/Canada using the autism diagnostic observation schedule (ADOS) and the Autism Diagnostic Interview—Revised were not used in the diagnostic process applied in Iran. This shortcoming was compensated for by the extensive clinical experience by the child neurologist/child psychiatrist who was familiar with the core behaviours in autism stated by the American Academy of Pediatrics in its Embargo from 2007. The control group consisted of typically developed and healthy children showing no signs of neurodevelopmental disorders who were recruited from the same area as the children with ASD. Children who had any kind of infection/infectious disease within two weeks prior to the time of examination were excluded from this study.

The study was approved (MT/1247) by the ethics committee of the Iran University of Medical Sciences, Tehran.

6.1.2 Procedure 6.1.2.1 Blood Sample Collection

Blood samples were collected by a paediatric nurse, and those from the children diagnosed with autism were collected under the supervision of a child psychiatrist with special training in the field of childhood psychosis. Venous blood was collected into 3 mL EDTA tubes (Vacutainer System; Becton-Dickinson Inc., Plymouth, UK), and plasma was separated immediately thereafter by centrifugation at 1,300 g for 10 min at 4° C. Thereafter, an inhibitors cocktail (30 μL per 1 mL plasma) was added to the resultant plasma sample (cocktail inhibitor solution: 2.0 M Tris, 0.9 M Na-EDTA, 0.2 M Benzamidine, 92 μM E-64, and 48 μM Pepstatin; Sigma, St. Louis, Mich, USA). The plasma was stored at −80° C.

6.1.2.2 Assay

Figure 9:
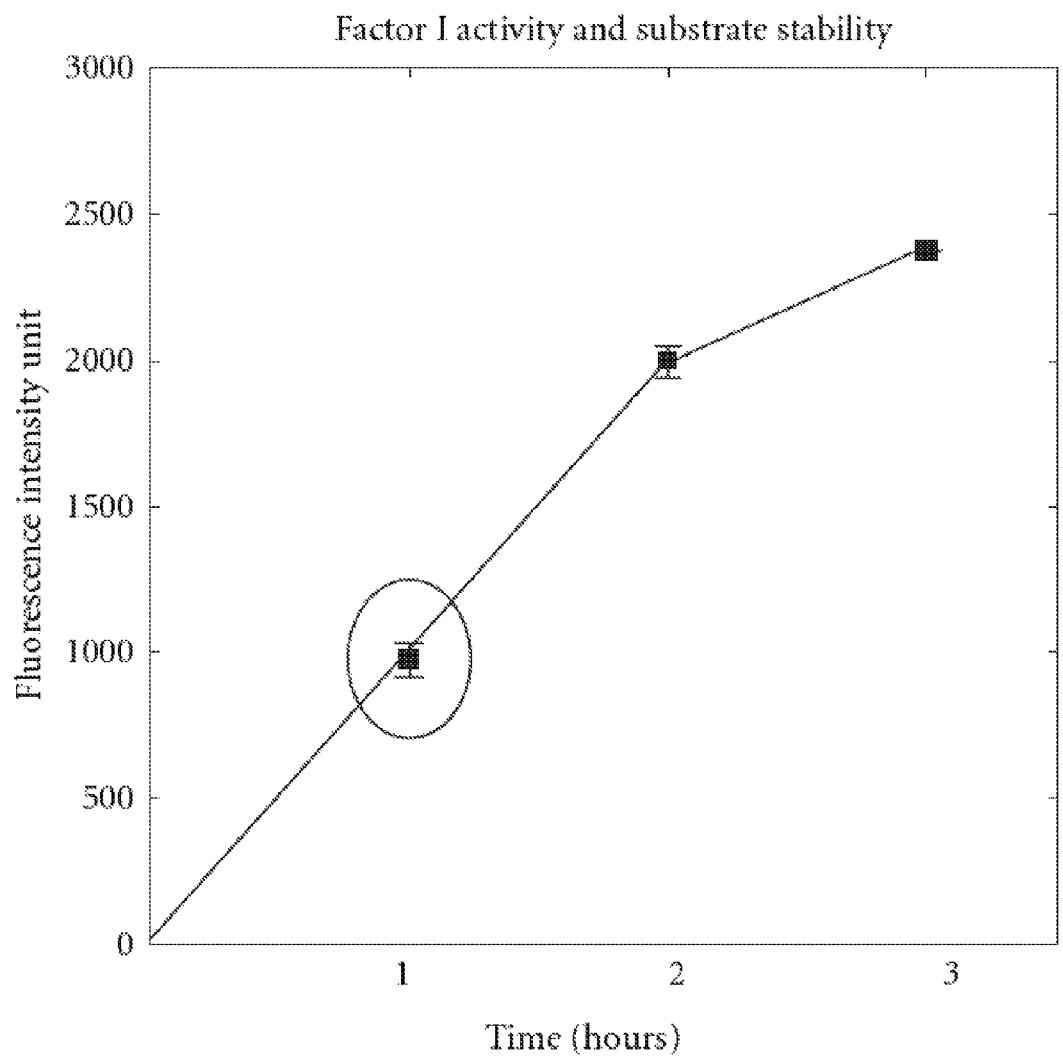
FIG. 9: Fluorescence intensity of release of 7-amino-4-methyl coumarin as a function of plasma incubation period (mean±SD; 1 h (974±44.2), 2 h (1995±45.2) and 3 h (2374±1.2)).

Methods based on the hydrolysis of fluorogenic substrates have previously been described by Tsiftoglou and Sim (Journal of Immunology, vol. 173, no. 1, pp. 367-375, 2004) and Gupta et al. (Journal of Autism and Developmental Disorders, vol. 26, no. 4, pp. 439-452, 1996). The following assay procedure was found to be optimal for assaying complement factor I (fI) activity in the plasma. 20 μL of plasma was incubated with 80 μL of buffer (100 mM phosphate buffer, pH 7.5, containing 1 mM EDTA, 1 mM DTT and 1 mM sodium azide) for 10 min at 37° C. to reach thermal equilibrium. 100 μL of substrate solution (200 μM Boc-Asp(OBz)-Pro-Arg-7-amino-4-methylcoumarin; Bachem, Bubendorf, Switzerland) in 25 mM phosphate buffer, pH 7.4, was then added, and the mixture was incubated at 37° C. for 60 min (see FIG. 9). The reaction was inhibited by the addition of 1 mL of 1.5 M acetic acid, and the release of 7-amino-4-methylcoumarin was measured by spectrofluorometer (Hitachi-f 2000; $\lambda_{ex}$: 360 nm; $\lambda_{em}$: 440 nm; slit width: 2.5). All measurements were carried out randomized and in duplicate. Background fluorescence in the assay was monitored by the use of plasma in the absence of substrate and was subtracted from values obtained in the presence of substrate.

6.1.3 Data Analysis and Statistics

Plasma fI activity was log-normally distributed, and logarithmic values were, therefore, used when analysing differences between the ASD group and the control group. To adjust for age (dichotomized using the median value, 5 years) and gender, factorial ANOVA was used. A value <0.05 was considered statistically significant. Statistica 8.0 (StatSoft©, Tulsa, Okla, USA) was used. Intra- and interassay variability of the plasma fI activity was expressed as the standard error of a single determination ($S_{method}$) using the formula:

$$S_{method} = \sqrt{\left(\frac{\Sigma d_i^2}{(2n)}\right)}, \quad (1)$$

where $d_i$ is the difference between the i:th paired measurement and n is the number of differences. The $S_{method}$ was expressed as the coefficient of variation (%).

6.2 Results

Figure 10A:
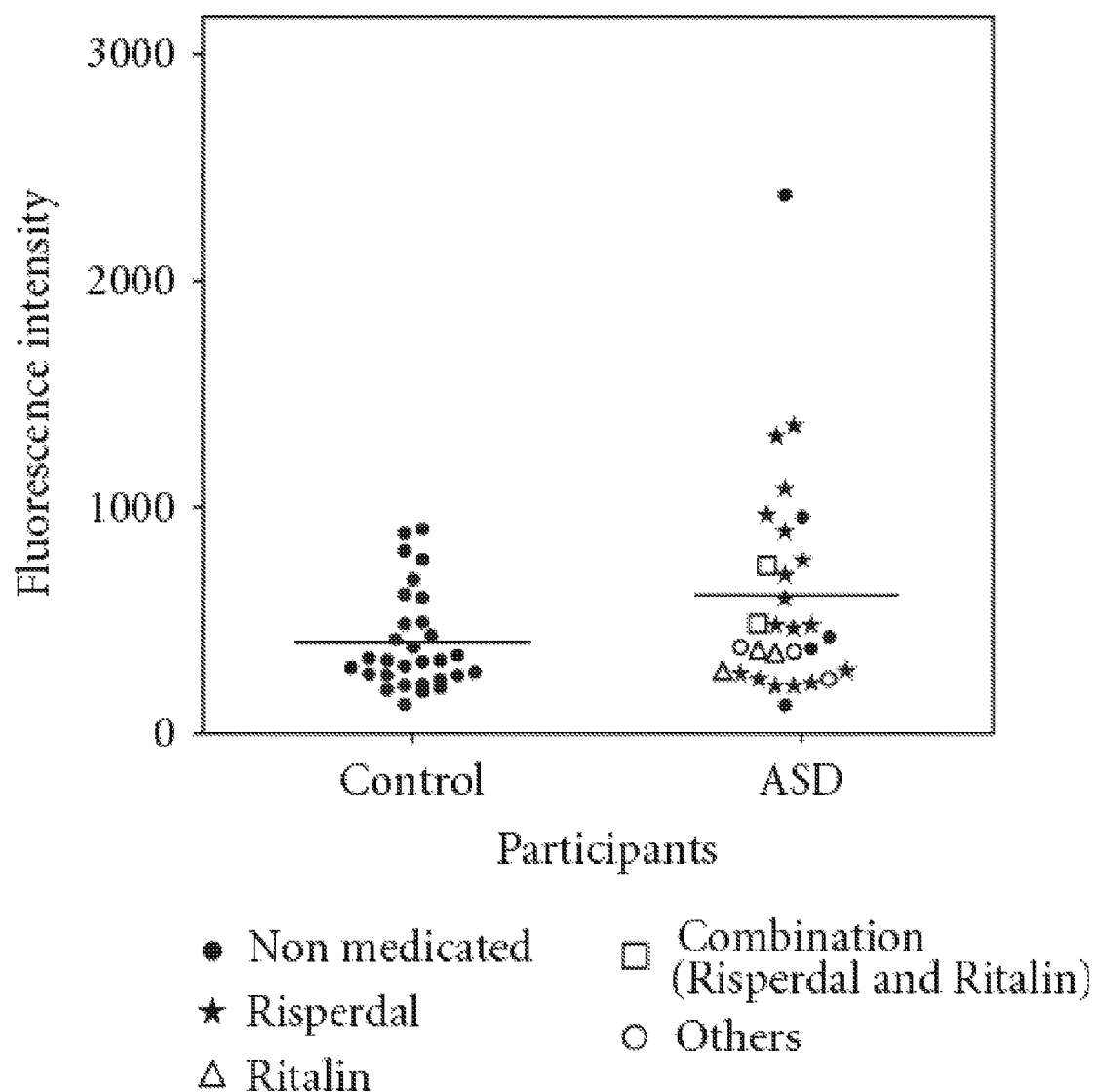
FIG. 10: (a) Complement factor I activity in EDTA plasma from children with autism spectrum disorder (ASD) (n=30) and healthy control children (n=30). A scatter plot of factor I activity for each individual is shown. Samples from ASD children who were not under medication at the time of the investigation, those under medication with Risperdal, Ritalin, a combination thereof, or other medications such as antipsychotics (thioridazine) or anticonvulsants (fenobarbital and sodium valproate) are shown. (b) Mean values and standard errors of the complement factor I activity in EDTA plasma are shown for the different age groups and genders for both children with ASD and the healthy control group. In the ASD group; age≤5 years: males (n=17), females (n=4) and age>5 years: males (n=6), females (n=3). In the healthy control group; age≤5 years: males (n=4), females (n=10) and age>5 years: males (n=9), females (n=7).

There was significantly higher activity of plasma fI in the children with ASD (geometric mean (95% confidence limit): 523 (154-1776) when compared with the control group: 361 (135-967; ANOVA P=0.015, adjusted for age and gender; FIG. 10a).

Figure 10B:
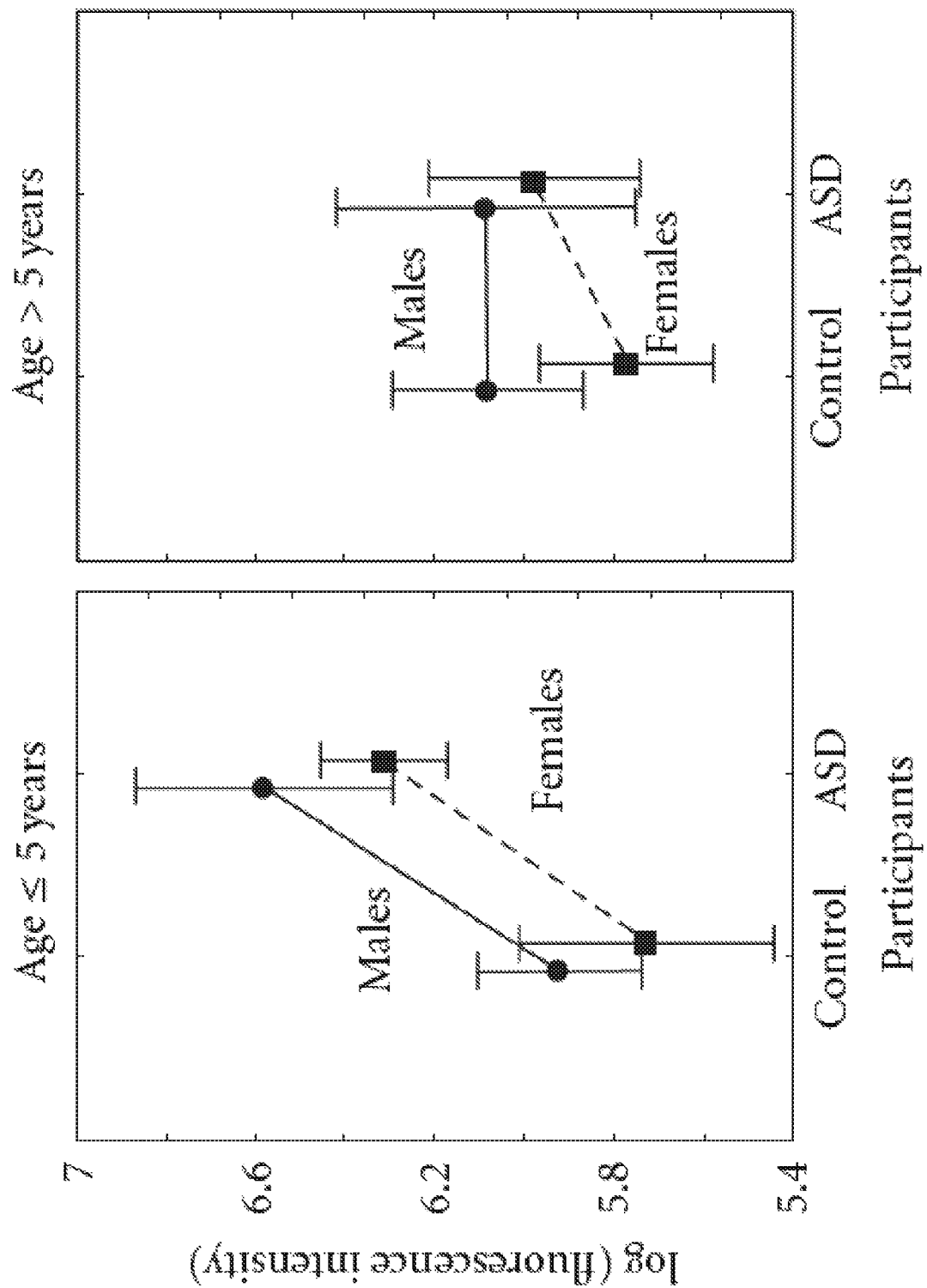

No statistically significant interactions were found with regard to gender and age, and no significant associations were found between fI activity and age or gender (ANOVA; p=0.25 for gender and 0.42 for the two age groups, FIG. 10b). In the ASD group, some children with severe autism were under medication with Risperdal to reduce hyperactivity and violent behavior, and a few were under medication with Ritalin to improve attention (Table V). It would have been ethically questionable to discontinue medication with the purpose of controlling the experimental design. We have correlated the data shown in FIG. 10a with the type of medication the children in the ASD group were receiving. Although we did not see any clear correlation between medication and distribution for the scatter plot data, it cannot be excluded that some differences in the pattern may be influenced by medication.

The values were statistically significantly higher in the children with ASD, and there was a weak association with gender. No statistically significant differences were found, however, between the age groups.

The methodological intra-assay error was small, 0.5%. The interassay methodological error was 13%. We found a significantly higher complement factor I enzyme activity in children with ASD compared to the control group of around the same age. This is, as far as we know, the first report regarding dysfunction of fI activity in children with ASD. Although not statistically significant, males tended to exhibit higher fI activity than females, and the difference between the control group and the ASD group was more convincing amongst the younger children, as shown in FIG. 10. Due to fI's role as a regulating factor in the complement system pathway, an fI abnormality could play a role in the onset of ASD. A defect in this pathway makes the individual more vulnerable to various inflammations.

7. Treatment of Autism with a Complement Factor I Inhibitor

Suramin

Patients diagnosed with autism are treated with suramin, starting with 0.1 g per single weekly intravenous injection. Where necessary, the dose is escalated in increments of 0.1 g to up to 1 g per injection. Dosing is further adjusted individually by the supervising clinician. In cases of severe adverse effects, the dose is lowered or the treatment interrupted. The improvement of function is followed compared to baseline by weekly assessments under the paradigm described under 6.1.1 above. Significant improvements in functioning are observed during the course of the treatment compared to baseline.

FUT-175 (6-amidino-2-naphthyl p-guanidinobenzoate dimethanesulphonate)

Patients diagnosed with autism are treated orally with FUT-175. The dosing is initiated with 0.1 mg/kg/day (divided in two daily doses), and where necessary increased to 0.25 mg/kg/day (divided in two or four daily doses) and subsequently to 0.5 mg/kg/day (divided in four daily doses). Dosing is further adjusted individually by the supervising clinicial. The improvement of function is followed compared to baseline by weekly assessments under the paradigm described under 6.1.1 above. Significant improvements in functioning are observed during the course of the treatment compared to baseline.

Elafin

Patients diagnosed with autism are treated with elafin by intravenous injection, starting with 10 mg twice daily. Where necessary, the dose is escalated to 20, 100, 200 and then 400 mg per injection. Dosing is further adjusted individually by the supervising clinician. In cases of severe adverse effects, the dose is lowered or the treatment interrupted. The improvement of function is followed compared to baseline by weekly assessments under the paradigm described under 6.1.1 above. Significant improvements in functioning are observed during the course of the treatment compared to baseline.

a. providing a sample from the subject to be diagnosed;
b. determining the concentration of a peptide having the amino acid sequence NH₂—SSKITHRIHWE-SASLLR*—COOH (SEQ ID NO:1), wherein the C-terminal residue denoted with R* has a side chain as depicted in Formula (I):

in said sample; and
c. comparing said concentration to a reference value based on the concentration of the peptide in step b. in a similar sample from a healthy control subject;
 wherein a lower concentration than the reference value in the sample is indicative of the presence of an autism spectrum disorder.

The invention claimed is:

1. A method of diagnosis for an autism spectrum disorder, comprising the steps of:

2. The method of claim 1, further comprising the steps of
a. determining the concentration of a peptide with sequence:

SSKITHRIHWESASLLR (SEQ ID NO: 3)
and/or
SSKITHRIHWESASLL (SEQ ID NO: 2)

in said sample; and
b. comparing said concentration to a reference value based on the concentration of the same peptide(s) in a similar sample from a healthy control subject;
wherein a higher concentration than the reference value in the sample is further indicative of the presence of an autism spectrum disorder.

3. The method of claim 1, further comprising:
d. providing a second sample from the subject to be diagnosed;
e. determining the level of activity of complement factor I in said sample;
f. comparing said activity to a reference value based on the level of activity of complement factor I in a similar sample from a healthy control subject; wherein a higher activity than the reference value in the second sample is indicative of the presence of an autism spectrum disorder in the subject; and
g. aggregating the results of (c) and (f).

4. The method according to claim 1, wherein the biological sample is selected from the group consisting of: a blood sample, a plasma sample, heparinised plasma sample, EDTA-plasma sample, a serum sample, a urine sample, a saliva sample, a tear sample, a cerebrospinal fluid sample, an ascites sample, a tissue sample and a biopsy.

5. The method according to claim 1, wherein the biological sample is a heparinised plasma sample.

6. The method according to claim 1, wherein the determining is performed by means of a method based on mass spectrometry such as MALDI-TOF, SELDI-TOF, LC-MS or LC-MS/MS; or by means of an immunochemical assay, such as ELISA, RIA, FIA or DELFIA.

* * * * *